(12) United States Patent
Vaughn et al.

(10) Patent No.: US 6,528,097 B1
(45) Date of Patent: *Mar. 4, 2003

(54) SUSTAINED RELEASE NON-STEROIDAL, ANTI-INFLAMMATORY AND LIDOCAINE PLGA MICROSPHERES

(75) Inventors: William M. Vaughn, Silver Spring, MD (US); John E. Van Hamont, Ft. Meade, MD (US); Jean A. Setterstrom, Alpharetta, GA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/716,856

(22) Filed: Nov. 20, 2000

Related U.S. Application Data

(62) Division of application No. 08/675,895, filed on Jul. 5, 1996, now Pat. No. 6,217,911, which is a continuation-in-part of application No. 08/446,149, filed on May 22, 1995, now abandoned, which is a continuation of application No. 06/590,308, filed on Mar. 16, 1984, now abandoned.

(51) Int. Cl.[7] .......................... A61K 9/50; A61K 31/19; A61F 13/00
(52) U.S. Cl. ........................ 424/501; 424/422; 514/570
(58) Field of Search ................................ 424/501, 422; 514/570

(56) References Cited

U.S. PATENT DOCUMENTS 3,540,444 A  11/1970  Moreland .................... 128/173
3,773,919 A  11/1973  Boswell et al. ................ 424/19
3,788,315 A  1/1974   Laurens ................... 128/173 H (List continued on next page.)

FOREIGN PATENT DOCUMENTS

EP  0052510 B2  10/1994  ............. A61K/9/50

OTHER PUBLICATIONS

Gilding, Biodegradable polymers for use in surgery–polyglycolic/poly (ac c acid) homo–and copolymers: 1, Polymer, vol. 20, Dec. 1979, pp1459–1464.
Biotechnology News, Aug. 22, 1997, vol. 17, No. 20, Topical DNA vaccine elicits immune response.
Hall, et al., Purification and Analysis of Colonization Factor Antigen I, Coli Surface Antigen I, and Coli Surface ANtigen 3 Fimbriae from Enterotoxigenic Escherichia Coli, Journal of Bacteriology, Nov. 1989, p6372–6374, vol. 171, No. 11.
Evans, et al. Purification and Characterization of the CFR/I Antigen of Enterotoxigenic Escherichia coli, Infection and Immunity, Aug. 1979, p 738–748, vol. 25.
Karjalainen, et al., Molecular Cloning and Nucleotide Sequence of the Colonization Factor Antigen I Gene of Escherichia coli, Infection and Immunity, Apr. 1989, p1126–1130, vol. 57.
Jeyanthi, et al., Novel, Burst Free Programmable Biodegradable Microspheres For Controlled Release of Polypeptides, Proceedings Int. Symp. control Release Bioact. Mater. (1996) p351–352.
Yeh, A novel emulsification–solvent extraction technique for production of protein loaded biodegradable microparticles for vaccine and drug delivery, Journal of Controlled Release, 33 (1995) 437–445.

(List continued on next page.)

*Primary Examiner*—Russell Travers
*Assistant Examiner*—Michael A. Willis
(74) *Attorney, Agent, or Firm*—Elizabeth Arwine

(57) ABSTRACT

A controlled release microcapsule pharmaceutical formulation for burst-free, sustained, programmable release of a non-steroidal, antiinflammatory drug over a duration from 24 hours to 2 months, comprising: a non-steroidal, antiinflammatory drug and a blend of biocompatible, biodegradable poly (lactide/glycolide).

21 Claims, 7 Drawing Sheets

U.S. PATENT DOCUMENTS

| | | | | |
|---|---|---|---|---|
| 4,166,800 A | 9/1979 | Fong | | 252/316 |
| 4,384,975 A | 5/1983 | Fong | | 427/213.36 |
| 4,530,840 A | 7/1985 | Tice et al. | | 514/179 |
| 4,542,025 A | 9/1985 | Tice et al. | | 424/78 |
| 4,585,482 A | 4/1986 | Tice et al. | | 106/15.05 |
| 4,622,244 A | 11/1986 | Lapka et al. | | 427/213.32 |
| 4,637,905 A | 1/1987 | Gardner | | 264/4.3 |
| 4,675,189 A | 6/1987 | Kent et al. | | 424/490 |
| 4,798,786 A | 1/1989 | Tice et al. | | 435/177 |
| 4,835,139 A | 5/1989 | Tice et al. | | 514/15 |
| 4,863,735 A | 9/1989 | Kohn et al. | | 524/422 |
| 4,897,268 A | 1/1990 | Tice et al. | | 424/422 |
| 4,938,763 A | 7/1990 | Dunn et al. | | 604/891.1 |
| 4,941,880 A | 7/1990 | Burns | | 604/143 |
| 5,000,886 A | 3/1991 | Lawter et al. | | 264/4.3 |
| 5,019,096 A | 5/1991 | Fox, Jr. et al. | | 623/1 |
| 5,059,187 A | 10/1991 | Sperry et al. | | 604/290 |
| 5,064,413 A | 11/1991 | McKinnon et al. | | 604/70 |
| 5,075,109 A | 12/1991 | Tice et al. | | 424/88 |
| 5,102,872 A | 4/1992 | Singh et al. | | 514/21 |
| 5,129,825 A | 7/1992 | Discko, Jr. | | 433/90 |
| 5,133,701 A | 7/1992 | Han | | 604/289 |
| 5,236,355 A | 8/1993 | Brizzolara et al. | | 433/80 |
| 5,278,202 A | 1/1994 | Dunn et al. | | 523/113 |
| 5,290,494 A | 3/1994 | Coombes et al. | | 264/41 |
| 5,360,610 A | 11/1994 | Tice et al. | | 424/426 |
| 5,384,133 A | 1/1995 | Boyes et al. | | 424/501 |
| 5,407,609 A | 4/1995 | Tice et al. | | 264/46 |
| 5,417,986 A | 5/1995 | Reid et al. | | 424/499 |
| 5,429,822 A | 7/1995 | Gresser et al. | | 424/426 |
| 5,500,228 A | 3/1996 | Lawter et al. | | 424/486 |
| 5,538,739 A | 7/1996 | Bodmer et al. | | 424/501 |
| 5,639,480 A | 6/1997 | Bodmer et al. | | 424/501 |
| 5,643,605 A | 7/1997 | Cleland et al. | | 424/489 |
| 5,648,096 A | 7/1997 | Gander et al. | | 424/489 |
| 5,650,173 A | 7/1997 | Ramstack et al. | | 424/489 |
| 5,688,530 A | 11/1997 | Bodmer et al. | | 424/501 |
| 5,693,343 A | 12/1997 | Reid et al. | | 424/491 |
| 5,762,965 A | 6/1998 | Burnett et al. | | 424/499 |
| 5,811,128 A | 9/1998 | Tice et al. | | 424/501 |
| 5,814,344 A | 9/1998 | Tice et al. | | 424/501 |
| 5,820,883 A | 10/1998 | Tice et al. | | 424/501 |
| 5,853,763 A | 12/1998 | Tice et al. | | 424/489 |
| 6,217,911 B1 * | 4/2001 | Vaugn et al. | | 424/501 |

OTHER PUBLICATIONS

Yan, Characterization and morphological analysis of protein–loaded poly(lactide–co–glycolide) microparticles prepared by watewr–in–oil–in–water emulsion technique, Journal of Controlled Release, 32 (1994) 231–241.

Wang, et al., Influence of formulation methods on the in vitro controlled release of protein from poly (ester) microspheres Journal of Controlled Release, 17 (1991) 23–32.

Brown, Wonder Drugs' Losing Healing Aura, The Washing Post, Jun. 26, 1995, A section.

Setterstrom, Controlled Release of Antibiotics From biodegradable Microcapsules For Wound infection Control, Chemical Abstracts, 1983, pp215–226.

Perez–Casal, et al., Gene Encoding the Major Subunit of CS1 Pili of Human Enterotoxigenic Escherichia Coli, Infection and Immunity, Nov., 1990, p 3594–3600, vol. 58, No. 11.

Jordi, et al., Analysis of the first two genes of the CS1 fimbrial operon in human enterotoxigenic Escherichia coli of serotype 0139: H28, FEMS Microbiology Letters 80, (1991) p265–270.

Tan, et al., Mapping the Antigenic Epitopes of Human Dihydrofolate Reductase by Systematic Synthesis of Peptides on solid Supports, The Journal of Biological Chemistry, vol. 265, No. 14, Issue of May 15, pp. 8022–8026 (1990).

McConnel, et al., Antigenic homology within human enterotoxigenic Escherichia coli fimbrial colonization factor antigens: CFA/I, coli–surface–associated antigens (CS)1, CS2, CS4 and CS17, FEMS Microbiology Letters 61 (1989) 105–108.

Van der Zee, Efficient mapping and characterization of a T cell epitope by the simultaneous synthesis of multiple peptides, Eur. J. Immunol. 1989, 19: 43–47.

Cassels, et al., Analysis of Escherichia coli Colonization Factor Antigen I Linear B–Cell Epitopes, as Determined by Primate Responses, following Protein Sequence Verification, Infection and Immunity, Jun. 1992, p. 2174–2181, vol. 60, No. 6.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70–85 (1992).

Brown, A hypothetical model of the foreign antigen biinding site of Class II histocompatibility molecules, Nature, vol. 332, Apr. 28, 1988, p845–850.

* cited by examiner

SUSTAINED RELEASE NON-STEROIDAL, ANTI-INFLAMMATORY AND LIDOCAINE PLGA MICROSPHERES

CROSS-REFERENCE

This application is a divisional application of U.S. patent application Ser. No. 08/675,895 filed Jul. 5, 1996, U.S. Pat. No. 6,217,911 which is a continuation-in-part of U.S. patent application Ser. No. 08/446,149, filed May 22, 1995, now abandoned, and in corporates in its entirety, the contents of Ser. No. 08/446,149, which is a continuation of U.S. patent application Ser. No. 06/590,308 filed Mar. 16, 1984 now abandoned.

GOVERNMENT INTEREST

The invention described herein may be manufactured, licensed and used by or for governmental purposes without the payment of any royalties to us thereon.

FIELD OF THE INVENTION

This invention relates to providing novel pharmaceutical compositions for local delivery and sustained release of non-steroidal, anti-inflammatory drugs (NSAIDS) from biocompatible, biodegradable poly(DL-lactide-co-glycolide) (PLGA) microspheres. The resulting product is applied locally into soft tissues surrounding a surgical incision or traumatic wound site where it will locally sustain release of the NSAID.

The invention also relates to providing novel pharmaceutical compositions for local delivery and sustained release of lidocaine PLGA microspheres.

BACKGROUND OF THE INVENTION

Non-steroidal anti-inflammatory drugs (NSAIDS) have been effective in reducing inflammation and inducing analgesia; however, the conventional oral dosage forms of these drugs characteristically have short half-lives and irritate the gastrointestinal mucosa. Further, currently available slow release oral dosage forms, such as Biovail (enteric coated, double-layer tablets which release the drug for 12–24 hours) still result in inefficient systemic delivery of the drug and potential gastrointestinal irritation.

Therefore, currently available slow release oral dosage forms of NSAIDs induces systemic effects and the drug is not efficiently used at the site of inflammation.

Further, in the currently available slow release oral dosage forms of NSAIDs, fillers or additives are needed in order to accelerate or retard drug release.

Further still, large doses of NSAIDs administered by conventional dosing regimens often times result in toxicity and secondary pathology such as gastrointestinal tissue irritation.

Several publications and patents are available for sustained release of active agents from biodegradable polymers, particularly, poly(lactide/glycolides) (PLGA). Prior usages of PLGA for controlled release of polypeptides have involved the use of molar ratios of lactide/glycolide (L/G) of 75/25 to 100/0 for molecular weights >20,000. Further, prior art preparations of PLGA utilized fillers or additives in the inner aqueous layer to improve stability and encapsulation efficiency and/or to increase the viscosity of the aqueous layer, thereby modulating polymer hydrolysis and the biologically active agent or polypeptide release.

In addition, the prior art use of PLGA copolymers were end-capped, in that the terminal carboxyl end groups were blocked. In these end-capped co-polymers, the microcapsule preparations exhibited a low to moderate burst release of ~10–14% of the entrapped polypeptide in the first 24 hours after placement in an aqueous physiological environment. In part, these characteristics are due to the use of fillers in the inner aqueous phase. Further, a 1-month release of polypeptide is known with the use of a 75/25 co-polymer of PLGA of Mw <20,000.

Investigations in controlled release research has been proceeding especially to obtain a 1–2 month delivery system for biologically active agents or polypeptides using poly (lactide/glycolide) polymers. However, most of these systems have one or more of the following problems: poor encapsulation efficiency and large 'burst release' followed by an intermediate 'no release' or 'lag phase' until the polymer degrades. In general, release from these polymers occur over a period from about 4 weeks to about several months. In addition, in order to achieve this release a 50/50 co-polymer of Mw>30,000 or a 75/25 co-polymer of Mw>10,000 are employed which often results in residual polymer remaining at the site of administration long after the release of active core.

SUMMARY OF THE INVENTION

This invention provides novel pharmaceutical compositions for local delivery and sustained release of non-steroidal, anti-inflammatory drugs (NSAIDs) from biocompatible, biodegradable poly(DL-lactide-co-glycolide) (PLGA) microspheres. The resulting product is applied locally into soft tissues surrounding a surgical incision or traumatic wound site where it will locally sustain release the NSAID. In the context of this invention, ketoprofen, is preferred. Ketoprofen is an important non-steroidal anti-inflammatory drug, and is formulated into a drug delivery system that releases the drug in an aqueous solution or soft tissue for 7–60 days, depending upon its formulation.

The invention also provides novel pharmaceutical compositions for local delivery and sustained release of lidocaine PLGA microspheres.

One object of the invention is to provide biodegradable PLGA microspheres for sustained delivery of NSAIDs.

Another object of the invention is to provide sustained, local delivery of NSAIDs, for durations greater than 24 hours and for up to 2 months from a single dose.

A further object of the invention is to provide NSAID-loaded microspheres suitable for use as or incorporation with pulp capping materials in dental restoratives.

A still further object of the invention is to provide NSAID-loaded microspheres suitable for incorporation in bioadhesives or gel formulations to be used in wound or trauma sites and as an oral bandage for painful mouth lesions.

A yet further object of the invention is to provide oral dosage forms incorporating compositions of NSAID-loaded micropheres of this invention to deliver the microspheres to the gastrointestinal lumen where they can be adsorbed within the epithelium and sustain release their contents systemically.

A further object yet still of the invention is to provide the benefits of local pain obtusion and thereby allow for decreased dosing of the systemic medications such as broad action opioids.

A further object yet still is to provide sustained released lidocaine PLGA microspheres for the treatment of dental pain.

In general the excipients used in the PLGA formulation have molar compositions ranging from 100/0 to 50/50 lactide/glycolide with molecular weights of 10–100 kDa. In addition, two forms of the PLGA can be employed; namely: 1) the more hydrophobic end-capped polymer with the terminal residues functionalized as esters; and 2) the more hydrophillic uncapped polymer with the terminal residues existing as carboxylic acids.

The NSAID-loaded microspheres are prepared by two distinct processes, solvent evaporation and solvent extraction.

In the solvent evaporation process, the NSAID and PLGA were dissolved in a volatile organic solvent, preferably methylene chloride, and dispersed in an aqueous phase containing an emulsion stabilizer. Evaporation of the organic phase gave NSAID-loaded microspheres. Depending on processing parameters, the microspheres released the NSAID for a duration of 2 weeks to 2 months with minimal burst release.

In the solvent extraction process for preparing the NSAID-loaded microspheres, the NSAID and PLGA were dissolved in a polar organic solvent, preferably acetonitrile, which was dispersed in a non-polar organic phase, preferably mineral oil. The emulsion produced was then poured into a hydrocarbon solvent, preferably heptane. As the polar organic phase was extracted into the hydrocarbon, the microspheres formed. The microspheres produced released NSAID for 7 to 10 days displaying near zero-order kinetics.

In the case when the NSAID is ketoprofen, in both the solvent evaporation process and the solvent extraction process, the microspheres obtained contained 1–20% ketoprofen (w/w).

DETAILED DESCRIPTION OF THE INVENTION

This invention relates to the design of biocompatible and biodegradable microspheres for novel, sustained release of non-steroidal, anti-inflammatory drugs, including ketoprofen, over a period of up to 60 days in an aqueous physiological environment with little or no burst release.

Unlike currently available release systems which rely on the use of filler/additives such as gelatin, albumin, dextran, pectin, polyvinyl pyrrolidone, polyethylene glycol, sugars, etc., and are still prone to low encapsulation efficiencies and "burst effects", this invention achieves high encapsulation efficiency and 'burst-free' release without the use of any additive. In this invention, 'burst-free', programmable sustained release is achieved.

The excipients used in the formulation (PLGA) have molar compositions ranging from 100/0 to 50/50 lactide/glycolide with molecular weight of 10–100 kDa.

Additionally, two forms of the biocompatible, biodegradable poly(DL-/lactide-shield-glycolide) can be employed, one being the more hydrophobic end-capped polymer with the terminal residues functionalized as esters, and the other being the more hydrophillic uncapped polymer with the terminal residues existing as carboxylic acids.

The two forms of the PLGA used to prepare the NSAID-loaded microspheres are prepared by two distinct processes, solvent evaporation and solvent extraction.

EXAMPLE 1

Ketoprofen and PLGA were dissolved in methylene chloride, and dispersed in an aqueous phase containing an emulsion stabilizer. Evaporation of the organic phase gave ketoprofen-loaded microspheres, as is shown in FIGS. 1, 3, 4, and 5. The microspheres release ketoprofen for a duration of two weeks to two months with minimal burst release as can be seen from the foregoing referred to figures.

While methylene chloride is the preferred volatile organic solvent, any pharmaceutically acceptable volatile organic solvent will suffice in the context of this invention. Similarly, while ketoprofen is the preferred non-steroidal, anti-inflammatory drug, any pharmaceutically acceptable non-steroidal, anti-inflammatory drug will work in the context of the invention utilizing the solvent evaporation process.

EXAMPLE 2

Figure 2:
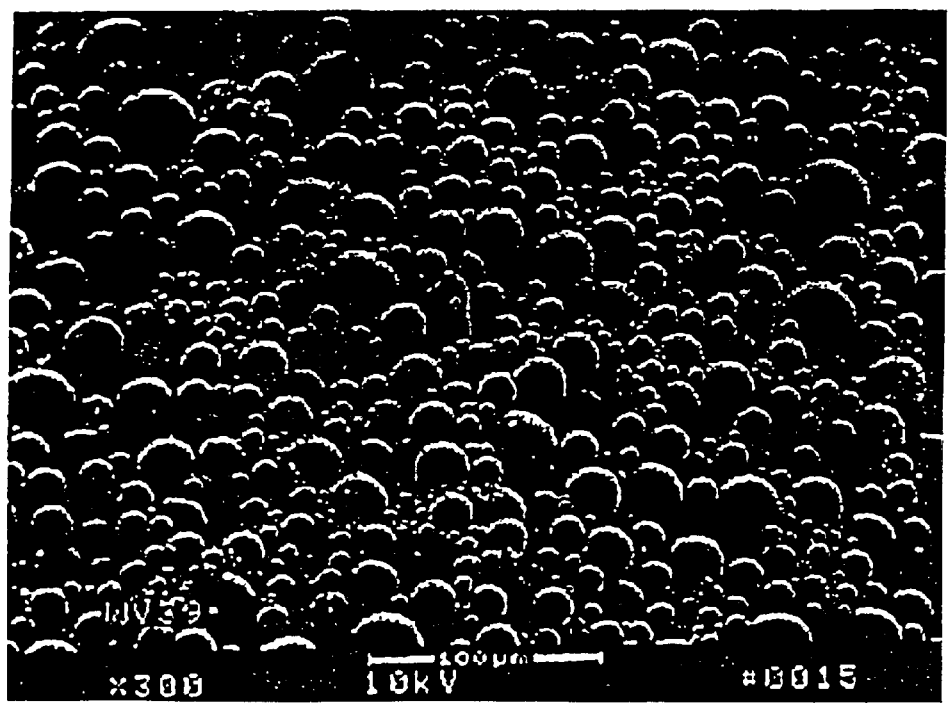
FIG. 2 shows a scanning electron micrograph of ketoprofen-PLGA microspheres prepared by the solvent extraction process.
Figure 3:
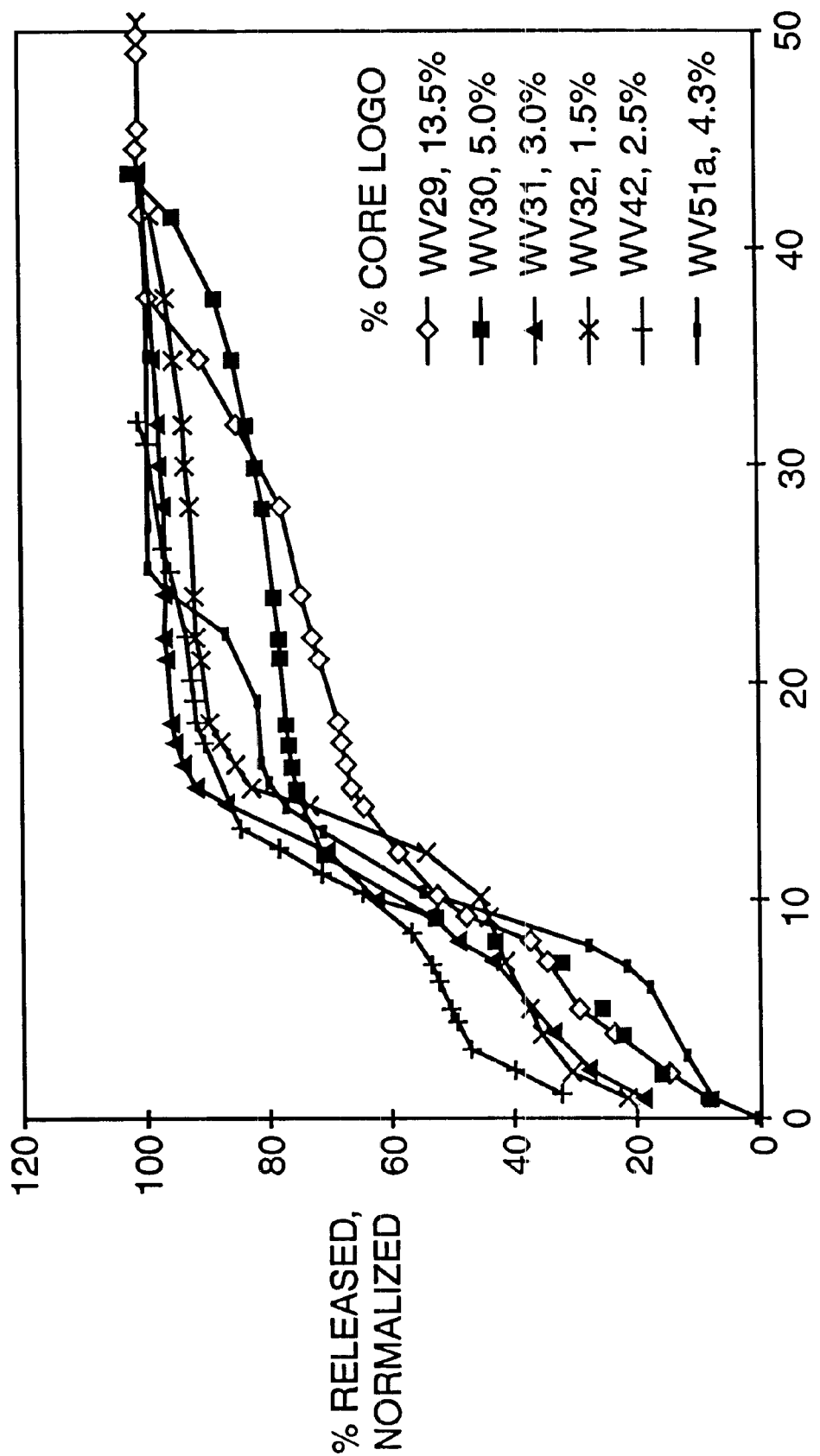
FIG. 3 shows ketoprofen release profiles from PLGA microspheres prepared by solvent evaporation. The release profiles are biphasic with a slower release in the first week followed by a more rapid release during the second week.
Figure 4:
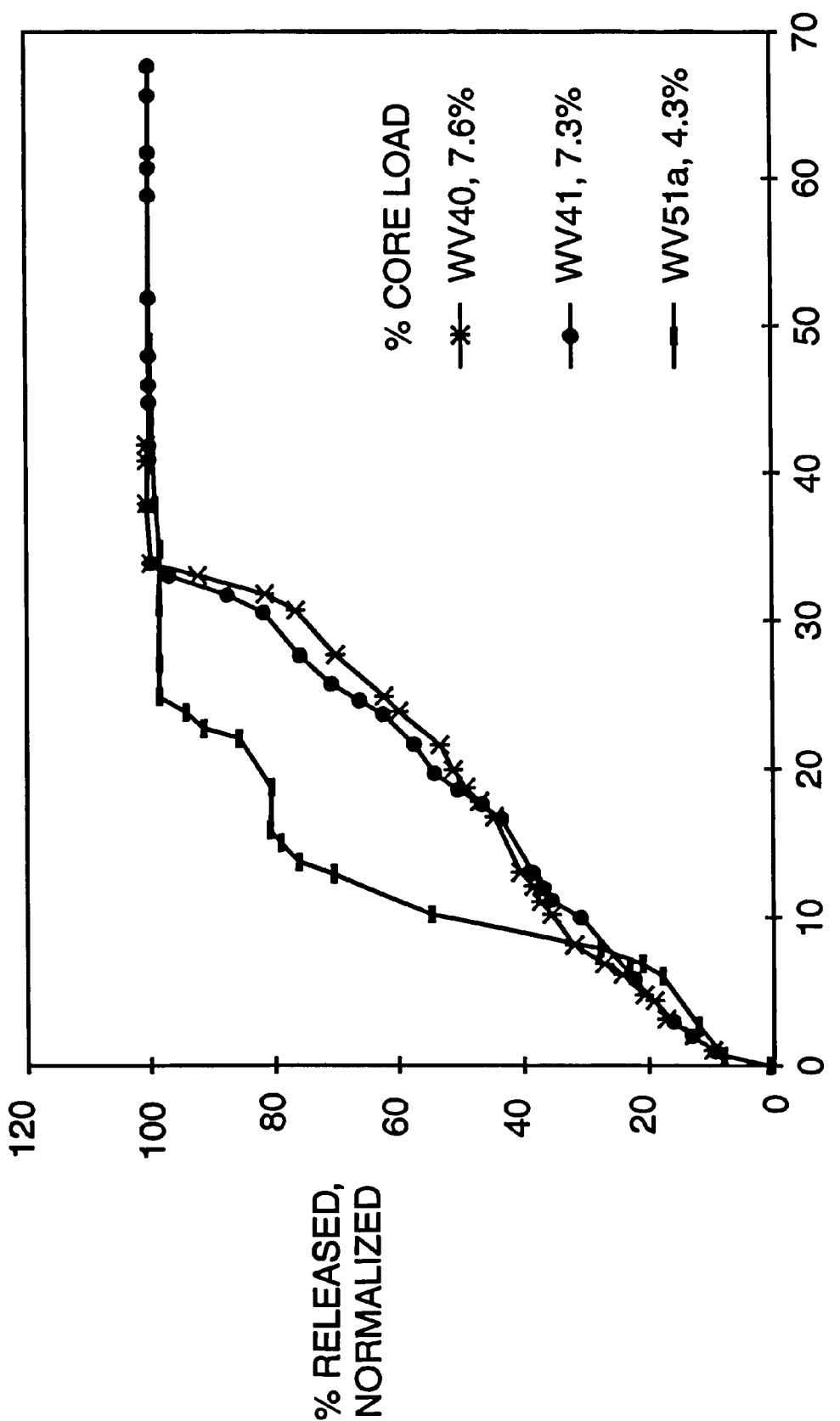
FIG. 4 shows ketoprofen release profiles from PLGA mirospheres prepared by solvent evaporation with increased initial polymer concentrations. A zero-order release of ketoprofen over 33 days is obtained. WV51a was prepared at reduced PLGA concentrations.
Figure 5:
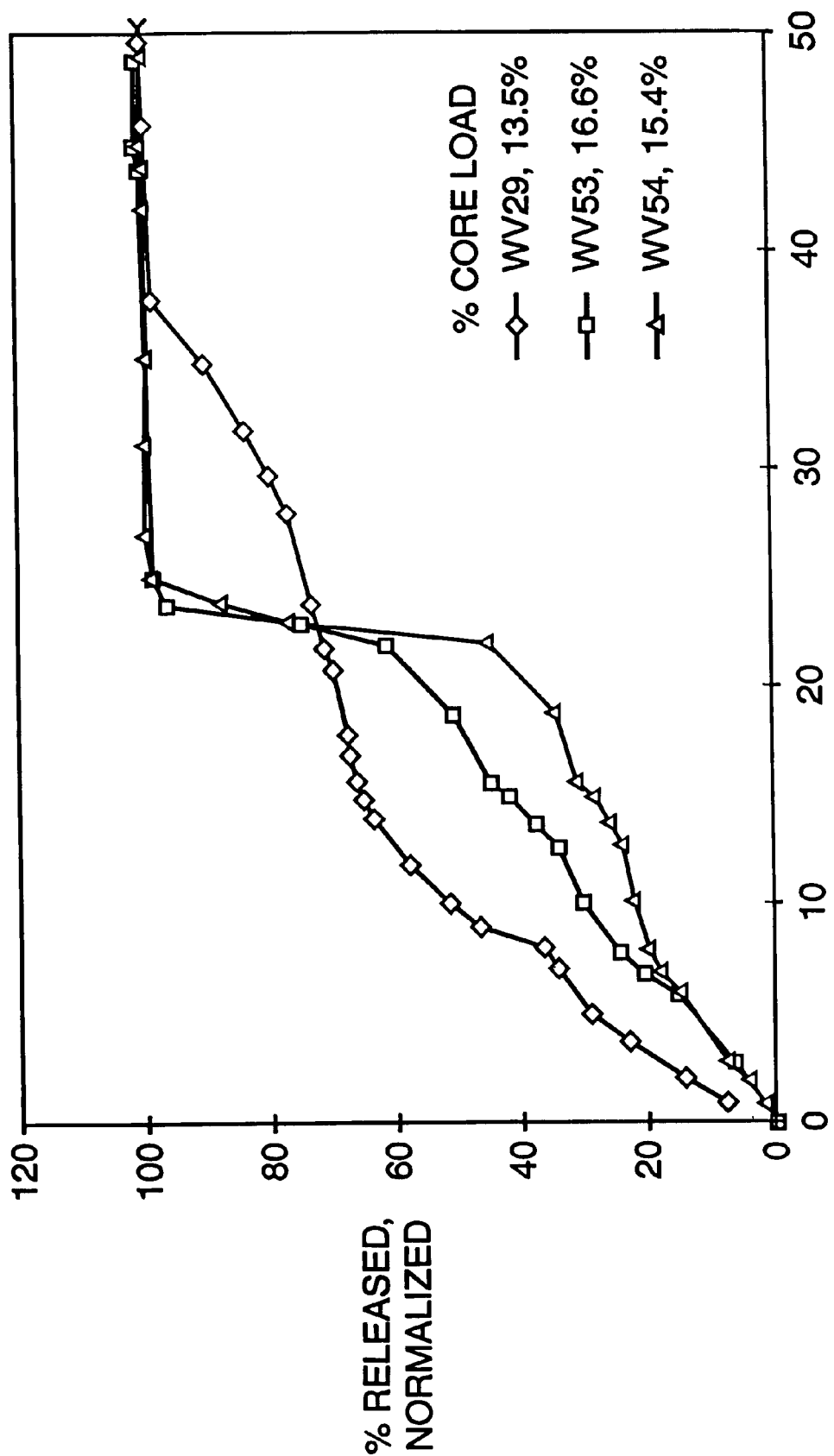
FIG. 5 shows ketoprofen release profiles from PLGA microspheres prepared by solvent evaporation at 40° C. demonstrating a zero-order release of 40–60% of the loaded ketoprofen followed by a terminal burst release of the remaining drug. WV29 was prepared at 20° C.
Figure 6:
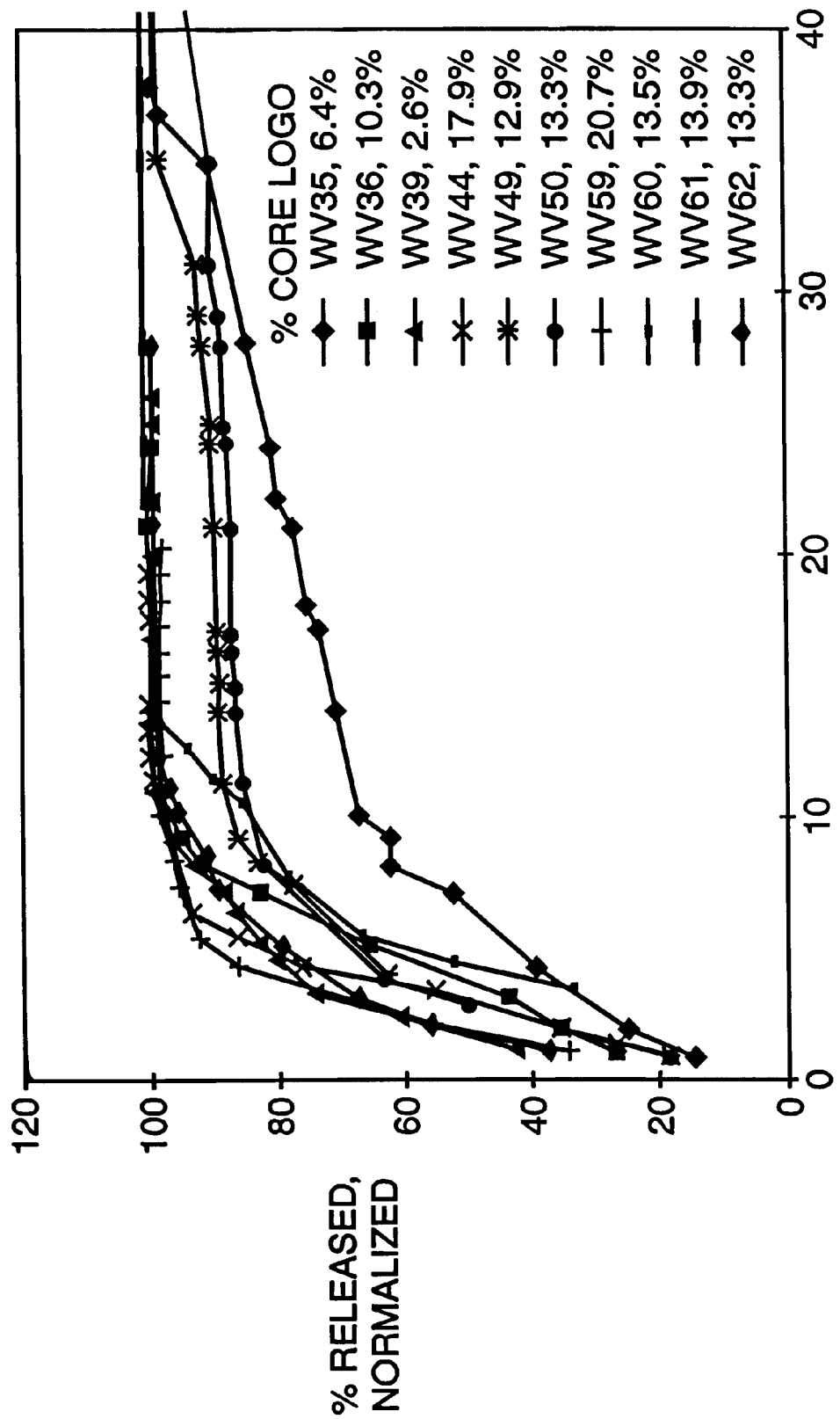
FIG. 6 shows ketoprofen release profiles from PLGA microspheres prepared by solvent extraction demonstrating 7–10 day release.

In the solvent extraction process, ketoprofen and PLGA were dissolved in acetonitrile, which is a polar organic solvent, and the mixture of ketoprofen, PLGA and acetonitrile is then dispersed in a mineral oil; however, any non-polar organic phase other than mineral oil will suffice in the context of the invention, even though mineral oil is preferred. The emulsion produced is then poured into a hydrocarbon solvent, preferably heptane. As the mineral oil phase was extracted into the heptane, microspheres of PLGA and ketoprofen are formed. The microspheres produced release ketoprofen for seven to ten days displaying near zero-order kinetics. Microspheres produced using this solvent extraction process are shown in FIGS. 2 and 6.

It was found that, using both methods of the invention, microspheres were obtained that contain 1–20% ketoprofen (w/w).

The NSAIDs are prescribed for arthritic conditions to reduce pain and delay debilitating inflammation, and a single, localized dose into joints lasting 2–3 months is very advantageous. Further, the microspheres of the invention are suitable for incorporation into a number of delivery vehicles to provide sustained release of a NSAID-loaded for many other applications for the treatment of mild pain and inflammation.

In this connection, one important use of the microspheres of the invention is in the use in dentistry as pulp capping agents to treat pulping pain (pulpalgia) and pulpalgia inflammation (pulpitis) better known as toothache associated with carious lesions or tooth trauma. The microspheres of the invention may also be used post operatively following tooth extractions to limit painful, inflammatory responses. Such application can be used in conjunction with systemic pain alleviating medications to control chronic intractable pain with the benefit that local pain obtusion will follow for decreased amounts of systemic medication.

Acute dental pain due to decay or trauma is a significant cause (21% of sick calls) of lost duty time for military personnel that impacts on combat readiness. Soldiers presenting with inflammation of the dental pulp would benefit from non-steroidal, anti-inflammatory drug (NSAID) pulp capping materials. Pulp capping materials are often used when the pulp is inflamed or exposed due to large carious lesions or facial trauma. Reduction of the inflammatory response decreases pain and possible pulpal necrosis. Successful use of NSAID pulp capping materials in far-forward dental treatment assist in providing a pain-free recovery, eliminate need for endodontic therapy, and allow for the immediate return to duty of soldiers.

The microencapsulation of ketoprofen in polylactic-glycolic acid (PLGA) meets these demands.

EXAMPLE 3

As mentioned microspheres of ketoprofen and 50/50 PLGA, (i.v. 0.66–0.80 dl/g) were prepared by two methods, solvent evaporation or solvent extraction. By solvent evaporation, ketoprofen and PLGA were dissolved in methylene chloride, and an o/w emulsion was prepared by stirring the organic phase in an aqueous 1% polyvinyl alcohol solution (31k–50k g/mol). Evaporation of the volatile $CH_2Cl_2$ resulted in the precipitation of ketoprofen-PLGA microspheres.

EXAMPLE 4

By the solvent extraction method, ketoprofen and polymer were dissolved in acetonitrile, and a w/o emulsion was prepared in mineral oil by agitation with a Silverson mixer. The emulsion was then poured into a large volume of stirring heptane, and a drug-polymer microspheres precipitated as the acetonitrile diffused into the heptane.

The particle size distributions of resulting microsphere formulations were determined by optical microscopy, and surface morphologies were determined by scanning electron microscopy. The drug content of the microspheres was determined by dissolving a sample in acetonitrile, and the ketoprofen was quantified by reverse phase HPLC using a Spherosob ODS-2, 5u column (4.6×250 mm) and a 20/80 acetonitrile/0.2M sodium phosphate dibasic solution mobile phase with a 1/ml/min flow rate.

Ketoprofen release profiles were determined in vitro for the PLGA microspheres. Microspheres were suspended in 1 ml phosphate buffer solution maintained at 37±1° C. in a shaker bath. The buffer was removed and refreshed over time. The ketoprofen concentration was determined by HPLC.

Figure 1:
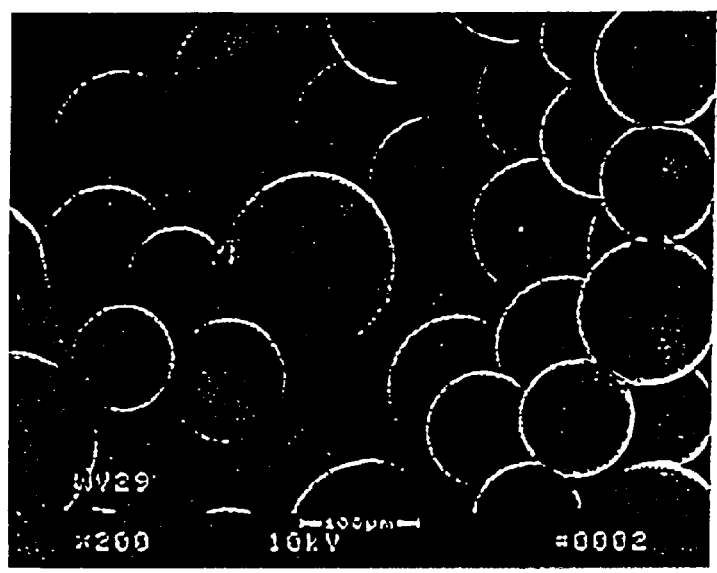
FIG. 1 shows a scanning electron micrograph of ketoprofen-PLGA microspheres prepared by the solvent evaporation process.

Microencapsulation of ketoprofen by solvent evaporation gave product yields of 65–80%. The volume mean diameters of formulations ranged from 73–108 um with narrow polydispersities, and SEM analysis showed that the microspheres were smooth, non-porous spheres (FIG. 1).

Ketoprofen contents ranging from 4–10% by weight were achieved with only 20–30% loading efficiencies. These modest loading efficiencies appear to be due to the aqueous solubility of ketoprofen (4 mg/ml), and the drug diffused into the aqueous phase when stirred overnight. Reducing the evaporation time to 8 hours increased loading efficiencies to 50–60%, however the spheres aggregated due to residual solvent.

Preliminary attempts to increase the core loading efficiencies by decreasing the time needed to completely evaporate the methylene. chloride were promising. Increasing the PLGA concentration of the dispersed phase from 100 mg/ml to 250 mg/ml increased loading efficiencies to 65–75%. Heating the o/w emulsion to 50° C. for 2 hours increased-the efficiency to 75–85%.

The microencapsulation of ketoprofen by solvent extraction was investigated to achieve greater core loading efficiencies. Microspheres with ketoprofen contents from 10.3% to 17.9% (20% theoretical) were prepared with an average of 68% loading efficiency (range, 53–94%). Typical number and volume average diameters were 20 um and 5 um, respectively. SEM analysis showed the microspheres to be smooth, solid spheres. The solid microspheres obtained differ from previous solvent extraction formulations of lidocaine hydrochloride-PLGA formulations that were porous.

Characteristically, ketoprofen-PLGA microspheres prepared by solvent evaporation slowly released 25–35% of their contents during the first week. This release was followed by an accelerated release of the remaining drug during the next 7–10 days. After 50 days, the hydrated microspheres had not significantly degraded.

Factors contributing to the lag time before significant release was observed include the high molecular weight (70k–100k g/mol) and hydrophobic nature of the PLGA resulting in slow hydration of the microspheres. Also, SEM analysis showed product spheres to be relatively free of defects reducing the possibility of a burst release. Similar profiles of an accelerated release beginning at 7–10 days were observed for lidocaine-PLGA formulations with the same polymer molecular weight. Release is independent of the core loading for this narrow range of 1.5–13.5%.

Heated solvent evaporation formulations (core loads: 7.6, 7.3%) demonstrate zero-order, more sustained release. At 30 days, only 30% of the ketoprofen is estimated to be released.

Ketoprofen-PLGA formulations prepared by solvent extraction show a steady and complete release of ketoprofen in 7–10 days (FIG. 6). The increased surface area of these smaller diameter microspheres contribute to the observed release. The near-linear release indicates the drug is evenly distributed throughout the PLGA matrix. Such release characteristics are highly beneficial for use as anti-inflammatory pulp-capping materials.

Ketoprofen and PLGA combined to form a miscible and homogeneous solid matrix of drug microspheres. This result affords steady and sustained ketoprofen release vehicles for potential use for localized inflammation. In relation to the treatment of pulpitis, plastic chambers are being used to model interactions between ketoprofen and dentin, inflamed pulpal tissue, and common pulp capping dressings such as calcium hydroxide.

While ketoprofen is preferred, any of the Non-steroidal Anti-Inflammatory Drugs would suffice for encapsulation within the context of the invention; exemplary of which are:
ibuprofen
flurbiprofen
aspirin
acetominophen
indocin
toradol
voltarin
tolectin
motrin A Clinical Trial to Evaluate Locally Applied Microencapsulated Ketoprofen in an Oral Surgery Model Introduction This study proposes to evaluate the safety, analgesic efficacy, and tissue response of locally applied ketoprofen [a non steroidal anti-inflammatory drug (NSAID)] that is encapsulated within small microspheres of the biodegradable polymer poly DL (lactide-co-glycolide). The response to encapsulated ketoprofen will be compared to a long-acting local anesthetic such as tetracaine, lidocaine, etidocaine, carbocaine, xylocaine, marcaine, nesacaine and etiod. Both drug formulations will be instilled into post-extraction sites immediately upon extraction of the tooth, but prior to the onset of pain (patients will be under the influence of local anesthetic during the extraction procedure). Subjects (n=84) will have two mandibular impacted third molars removed and be randomly allocated to receive one of six possible treatments placed into the resulting sockets: 0 mg (placebo formation), 3.125 mg, 6.25 mg, or 25 mg ketoprofen, or 50 mg bupivacaine. Each patient in these six groups (n=12/group) will also receive an oral placebo capsule. The seventh group of the subjects will receive a placebo applied at the extraction sites and 25 mg of ketoprofen orally. Subjects will remain at the clinic for six hours following drug administration. Every 30 minutes the offset of mandibular anesthesia, postoperative pain intensity, side effects, and recurrence of bleeding will be monitored. Demonstration of a dose-response relationship for ketoprofen at doses lower than needed for analgesia following oral administration will provide the basis for a follow-up study in which an optimal dose of ketoprofen will be combined with bupivacaine.

Project Goal and Scientific Justification

Approaches to suppress undesirable sequelae of the inflammatory process use drugs that interfere with the synthesis of inflammatory mediators. An example is the administration of nonsteriodal anti-inflammatory drugs (NSAIDs) to suppress prostaglandins and the subsequent pro-inflammatory actions they initiate such as sensitization of nociceptors and edema formation. Another approach suppresses receptor mediated effects of inflammatory mediators. For example, antihistamines block the effects of histamine by competitive blockade of receptors. While these strategies are clinically effective, the quest continues to find methods to control acute pain which do not involve the systematic liabilities of NSAIDs or opioids.

The introduction of NSAIDs for the management of acute and chronic pain has resulted in improved analgesia and decreased side effects; however, there remain drawbacks such as a relatively slow therapeutic onset when taken orally, a ceiling of efficacy, and side effects with chronic use (NSAIDs will produce small amounts of GI bleeding at therapeutic doses which can result in ulcers with chronic use in approximately 25% of individuals). An alternative to administering high systematic doses for greater efficacy and a likely way to eliminate side effects is to sustain release NSAIDs or other drugs at the site of injury thereby achieving high local concentrations. This proposed study will evaluate the local administration of an NSAID into tooth extraction sites to determine if such a localized effect can be demonstrated. If demonstrated, it will provide a basis for evaluating the peripheral effects of other putative inhibitors and antagonists of the inflammatory process using this or a similar approach. Despite advantages of NSAIDs for pain management, a therapeutic void remains for the management of pain with a drug modality that has rapid onset by non-parenteral routes of administration and greater efficacy than can be achieved with oral NSAIDs.

Patient Selection

Patients will be evaluated for third molar removal following receipt of referral indicating the need for extraction. Patients will complete a medical history form which will be reviewed with the patient and a complete medical history recorded in the medical record. A panoramic radiograph will be taken to confirm the need for the extractions. Patients whose past history indicates that they may not have had a physical exam in greater than five years will be evaluated by a staff physician prior to surgery.

Inclusion Criteria:
patients of either sex requiring the removal of two impacted mandibular third molars (partially bony or soft tissue impaction).
16 years of age or older
indicates willingness to undergo oral surgery with local anesthesia and intravenous midazolam only.
willing to return for the removal of the remaining maxillary third molars at a second appointment.

Exclusion Criteria:
history of allergy to ketoprofen, aspirin, or any NSAID
history of aspirin or NSAID-induced asthma
females of childbearing potential who are not practicing adequate contraception (use of oral contraceptives or abstinence plus a negative urine pregnancy test)
recent history or present signs of impairment of renal, hepatic, endocrine, pulmonary, cardiac, gastrointestinal, neurologic, or cerebral function.
psychiatric disorder which would make validity of response questionable.
having received an investigational drug within 30 days of this study.
of bilateral local anesthesia during surgery as evidenced by anesthesia or paresthesia of the lower lip postoperatively.
use of drugs which interact with NSAIDs such as aspirin, warfarin, probenecid, methotrexate, lithium and diuretics.

Randomization and Stratification of Treatments

The treatments will be randomly allocated using drug formulations supplied by the developer (USADRD, Walter Reed Army Institute of Research). The formulations will be supplied as sterile preweighed amounts of ketoprofen microspheres. The samples will be coded by number and assigned in consecutive order. Following each extraction, an appropriate amount of the microspheres will be placed into the socket, the extraction site sutured, and a gauze retained in place with biting force for one hour to promote hemostatis.

The administration of treatments prior to pain onset will prevent stratification based on the level of starting pain.

Limition to soft-tissue and partial boney impactions should result in a similar degree of tissue injury and resultant pain among patients.

Integration of Date Collection and the Clinical Procedure

Patients will have two lower third molars extracted in a parallel groups, double-blind study. The teeth extracted will be mandibular soft tissue or partial boney impactions removed under local anesthesia with 2% lidocaine with 1:100,000 epinephrine and midazolam (Versed) sedation. The adequacy of the nerve block will be assessed several minutes after administration by the presence of lower lip anesthesia ("lip sign") and no response to probing of the buccal mucosa over the teeth to be extracted. After the completion of the procedure, subjects will remain in recovery room for 60 minutes with gauze pads over the extraction sites to ensure hemostatis. The extraction sites will be examined at each observation postoperatively to determine that bleeding has stopped. Subjects will remain at the clinic for six hours from the end of surgery to assess the onset and intensity of postoperative pain. Analgesia, lower lip anesthesia, side effects, and hemostasis will be evaluated at 30 minute intervals. Subjects will be remedicated with a standard analgesic upon request but will be encouraged to complete at least two observations following the loss of local anesthesia. The "rescue" medication administered will vary based on patient's level of pain: 800 mg of ibuprofen for moderate pain, ibuprofen plus codeine or oxycodone for moderate to severe pain, and IM ketolac for servere pain and agitation. Patients will be dismissed from the clinic at the end of the observation period and instructed to call if any complications occur at the extraction site. Patients who do not return to the clinic will be contacted seven days following surgery to inquire about the occurence of any subjective symptoms suggestive of alveolar osteitis (dry socket).

Prior to initiating the proposed study, up to six patients will be administered 25 mg of microencapsulated ketoprofen as described above to determine the best method for administering the treatments, the feasibility of the experimental design and data collection procedures, and the patients' response to administration of the formulation into the extraction site. An additional six patients will receive 10, 15, and 50 mg (2 patients at each dose) of encapsulated ketoprofen as a dose range study to assess whether any unexpected adverse effects might occur if the drug is tolerated at the site of administration.

Hazards and Precautions

Participation in this study will entail the hazards normally associated with oral surgery, the administration of local anesthesia and parenteral sedation, and the risks unique to the administration of an NSAID and a local anesthesia directly into an extraction site.

Complications of Oral surgery: Possible complications commonly associated with the extraction of impacted third molars include alveolar osteitis, infection at the extraction site and adjacent tissue, perforation of maxillary sinus, damage to the teeth adjacent to the teeth being extracted, and transient or permanent anesthesia or paresthesia of the inferior alveolar or lingual nerve. The incidence of these adverse events is low and variable but averages about 10% of all patients treated. A rare complication associated with oral surgery is hairline fracture of the mandible.

Adverse Effects of Local Anesthesia: Few adverse effects are associated with the use of 2% lidocaine with 1:100,000 epinephrine. Rare complications associated with the use of local anesthesia for dental procedures include temporary facial paralysis, hematoma, inadvertent intravascular injection, or an allergic reaction. Temporary paralysis of the facial nerve will resolve in a few hours; a hematoma will persist for several days with eventual discoloration of the face followed by healing. The sequelae of an intravascular injection or an allergic reacion will be managed as dictated by the magnitude and duration of the response.

Adverse Effects of IV Midazolam: Midazolam has proven to be a very safe and effective drug for outpatient sedation procedures despite the incidence of adverse effects associated with its use in the original concentration (5 mg/ml) when the drug was introduced. Adverse effects associated with the use of this drug for outpatient sedation include drowsiness, psychomotor incoordination, transient respiratory depression, paradoxical excitation, hiccoughs, nausea, vomiting, hyperventilation, dizziness and blurred vision. The drug will be given in the 1 mg/ml concentration by slow intravenous infusion following the manufacturer's recommended rate of administration. Patients respiratory rate will be monitored during the procedure with a pulse oximeter and in the recovery area by a nurse taking periodic vital signs.

1. Dionne, R A, Tahara, M A, Rowan, J S: Peripheral administration of low dose ketoprofen is analgesic in oral surgery model. 7th World Congress on Pain, Paris, 1993

Adverse Effects of Microencapulated Ketoprofen: The adverse effects attributed to orally administered ketoprofen are similar to those associated with other NSAIDs: GI irritation and upset, and impairment of renal function with chronic administration. Administration of ketoprofen (the free drug form) into extraction sites in two previous studies done at NIDR was not associated with any detectable increase in localized adverse effects such as alveolar osteitis or infection in 50 subjects[1,2]. It is recognized that the administration of an NSAID into the extraction site prior to blood clot formation may result in an increase in postoperative bleeding due to the temporary inhibitory effects of NSAIDs on platelet aggregation. Direct administration of 30 mg of aspirin into the extraction sites following oral surgery has been reported not to produce any increase in bleeding episodes or alveolar osteitis[3]. Subjects will be observed for any signs of bleeding during the six hour observation period and prior to dismissal from the clinic. The presense of the encapsulation excipient DL (lactide-co-glycolide) may possibly be associated with an increase in the infection rate; however, since it is the same polymer used in biodegradable suture materials (which have a very low infection rate in other surgeries), it is considered unlikely.

1. Dionne, RA, Tahara, MA, Towan, JS: Peripheral administration of low dose ketoprofen is analgesic in oral surgery model. 7th World Congress on Pain, Paris, 1993
2. Gordon, SM, Tahara, MA, Rowan, JS,n Dionne, RA, Dubner, R: Comparative analgesic efficacy of peripherally versus orally administered ketoprofen gel. J Dent Res, In Press, 1994.
3 Moore, U J, Deymour R A, Rawlins, MD: The efficacy of locally applied aspirin and acetaminophen in postoperative pain after third molar surgery. Clin Pharmacol Therap 52:292–296, 1992.

Study Parameters

Demographic date will be collected from each patient to allow retrospective inspection of the comparability of the treatment groups in terms of sex, age, weight, and height. The comparability of the surgical procedure will be assessed by the mean duration of surgery, the oral surgeons's postoperative classification of the surgical procedure, the dose of local anestetic used, and the dose of midazolam used. Dependent measures of analgesia and adverse effects will be collected at 30 minute intervals postoperatively and continuing until the end of the observation period or when the patient remedicates.

Duration of Local Anesthesia: Subjects will be asked to "tap your lower lip" and select a term which best describes the sensation: numb, tingling, or normal. Subjects who are, not reporting at least paresthesia ("tingling") prior to drug administration will be excluded as will subjects who do not report the loss of anesthesia by four hours postoperatively. This approach is needed to ensure comparability among groups in the offset of local anestesia and was used in a previously pretreated study to result in three groups with very similar offset of local anesthesia[1].

1. Dionne, R A, Tahara, M A, Rowan, J S: Peripheral administration of low dose ketoprofen is analgesic in oral surgery model. 7th World Congress on Pain, Paris, 1993

Analgesia: A category scale for pain intensity will be administered at each observation with categories: no pain (0), slight pain (1), moderate pain (2), or servere pain (3). A 100 mm visual analog scale will also be adminstered with endpoints a "no pain" and "worse possible pain". Patients will be asked to pick the work and make a mark on the line which best describes the amount of pain that they may be experiencing.

Adverse effects: Subjects will be asked if they are experiencing any other effects from the medication at each observation period. The type of adverse effect will be recorded, the intensity of the effect categorized as mild, moderate, or servere, and the onset and duration estimated. The type and incidence of adverse effects for each group will be compared post hoc by Chi-square analysis.

Hemostasis/Postoperative Bleeding: Subjects will will be observed at each 30 minute observation for any signs of bleeding and prior to dismissal. Any bleeding observed will be classified as slight ooze, persistent ooze, bleeding controlled with pressure, or bleeding requiring intervention. The incidence of postoperative bleeding will be compared among groups by Chi-squate analysis.

Evaluation of Results: The efficacy of the treatments will be assessed by a repeated measures analysis of variance including observations starting from the loss of anesthesia in the majority of subjects. Initially, all subjects should be reporting "numb" on the anesthesia category scale. Over time, the number of subjects reporting "tingling" or "normal" lower lip will increase. It is assumed that by 120 minutes postoperatively most patients will be reporting loss of anesthesia as evidenced by reports of "tingling" or "normal". The observations to be included will start at the first time point where the majority of the patients report loss of anesthesia (approximately two hours postoperatively) until the end of the observation period (six hours postoperatively). Post hoc tests will also be used to determine which time points are significantly different from each other.

Qualification of the Investigators: This clinical trial is being performed at the National Institute for Dental Research, NIH under a Cooperative Research and Development Agreement with the US Army. Oral Surgery will be performed by third year residents from Georgetown University who have clinical privileges to perform oral surgury at the Clinic Center, National Institute of Dental Research. The research will be supervised by Dr. Dionne who has been a clinical investigator at NIDR for 15 years and has conducted numerous similar studies. Drs. Vaughan, Van Hamont, and Setterstrom have been involved in the preclinical development of the microencapsulated ketoprofen formulations.

Formulation of Lidocaine-PLGA Microspheres

Microsheres of lidocaine base (Sigma) or lidocaine hydrochloride (prepared by adding HCL to lidocaine base) and 50/50 PLGA, i.v. 0.66–0.80 dl/g) were prepared by two methods, solvent evaporation or solvent extraction.

EXAMPLE 5

By solvent evaporation, lidocaine base and PLGA were dissolved in methylene chloride, and an o/w emulsion was prepared by stirring the organic phase in an aqueous 1% polyvinyl alcohol solution (31k–50k g/mol). Evaporation of volatile $CH_2CL_2$ resulted in the precipitation of lidocaine-PLGA microsheres.

EXAMPLE 6

By the solvent extraction method, either lidocaine or lidocaine hydrochloride and polymer were dissolved in acetonitrile, and a w/o emulsion was prepared in mineral oil by agitation with a Silverson mixer. The emulsion was then poured into a large volume of stirring heptane, and drug-polymer microspheres precipitated as the acetonitrile diffused into the heptane.

The particle size distributions of resulting microsphere formulations were determined by optical microscopy, and surface morphologies were determined by scanning electron microscopy. The drug content of the microspheres. were determined by dissolving a sample in acetonitrile, and the lidocaine was quantified by reverse phase HPLC using a Column Engineering BUTYL 5 $\mu$m column (4.6×250 mm) and a 50/50 acetonitrile/0.2M sodium phosphate dibasic solution mobile phase with a 1 ml/min flow rate.

Lidocaine release profiles were determined in vitro for the PLGA microspheres. Microspheres were suspended in a phosphate buffer solution maintained at 37±1° C. in a shaker bath, and aliquots were taken during the release period. The lidocaine concentration was determined by HPLC as stated above.

Figure 7:
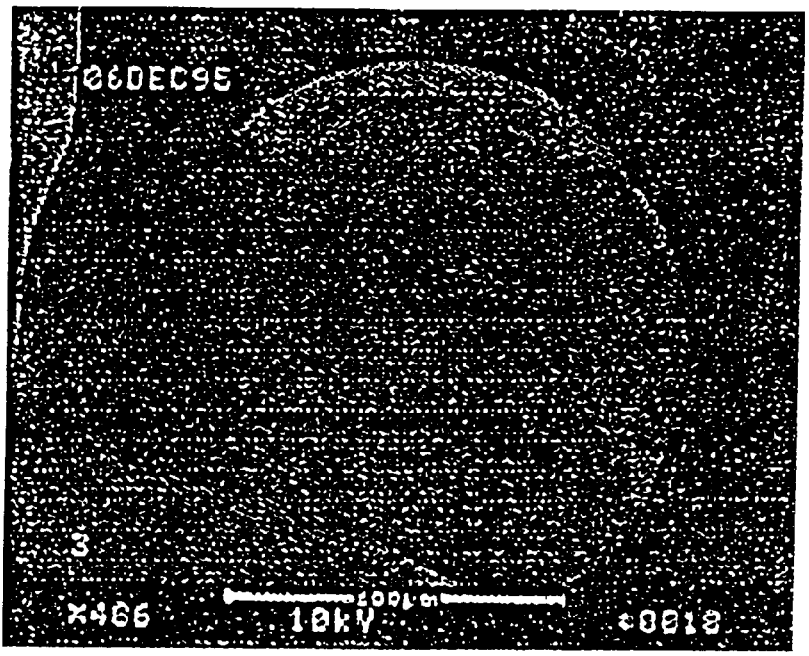
FIG. 7 shows lidocaine PLGA microspheres prepared by solvent evaporation. The volume mean diameters of formulations are from 120–135 $\mu$m with narrow polydispersites, and SEM analysis show that the microspheres were smooth, non-porous spheres.

Microencapsulation of lidocaine base by solvent evaporation gave product yields of 65–80%. The volume mean diameters of formulations ranged from 120–135 $\mu$m with narrow polydispersites, and SEM analysis showing that the microspheres were smooth, nonporous spheres (FIG. 7). Lidocaine contents ranging from 4–10% by weight were achieved with only 30–70% loading efficiencies. These modest loading efficiencies appear to be due to the aqueous solubility of lidocaine (4 mg/ml), and the drug simply diffuses into an aqueous phase. However increasing aqueous phase to pH 10 had no measurable effect on the loading efficiency.

Figure 8:
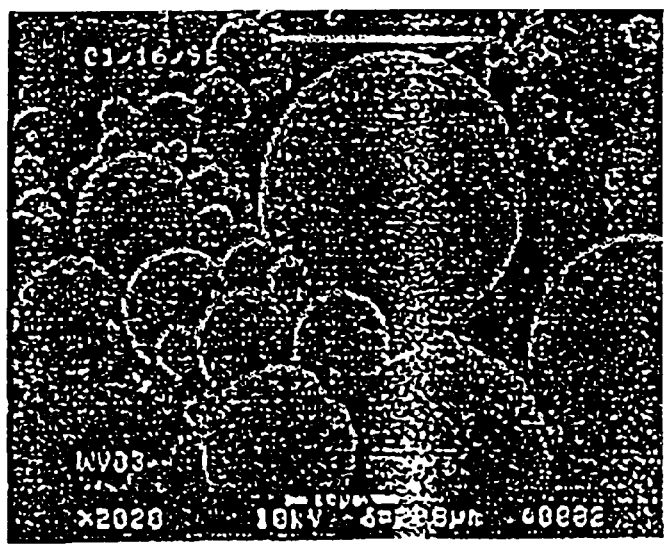
FIG. 8 shows lidocaine PLGA microspheres prepared by solvent extraction and having narrow distributions of 7–10 $\mu$m. SEM analysis showed the microspheres to be smooth and spherical but very porous.

The microencapsulation of lidocaine hydrochloride by solvent extraction was investigated to achieve greater core loading efficiencies. Indeed, microspheres with lidocaine contents from 5% to 20% were prepared with 100% loading efficiencies in all cases. Volume mean diameters for microspheres prepared by solvent extraction were 7–10 $\mu$m with narrow distributions. SEM analysis showed the microspheres to be smooth and spherical but very porous (FIG. 8). Attempts to encapsulate lidocaine base by solvent extraction resulted in poor loading efficiencies (10% or less).

Figure 9:
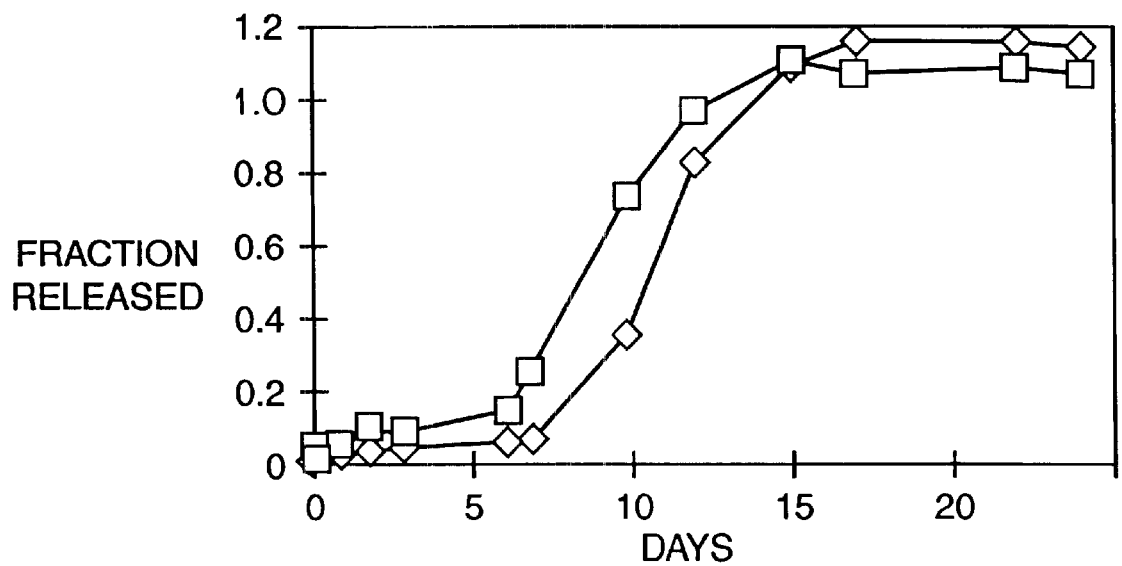
FIG. 9 shows release profiles of lidocaine-PLGA microspheres prepared by solvent evaporation.
Figure 10:
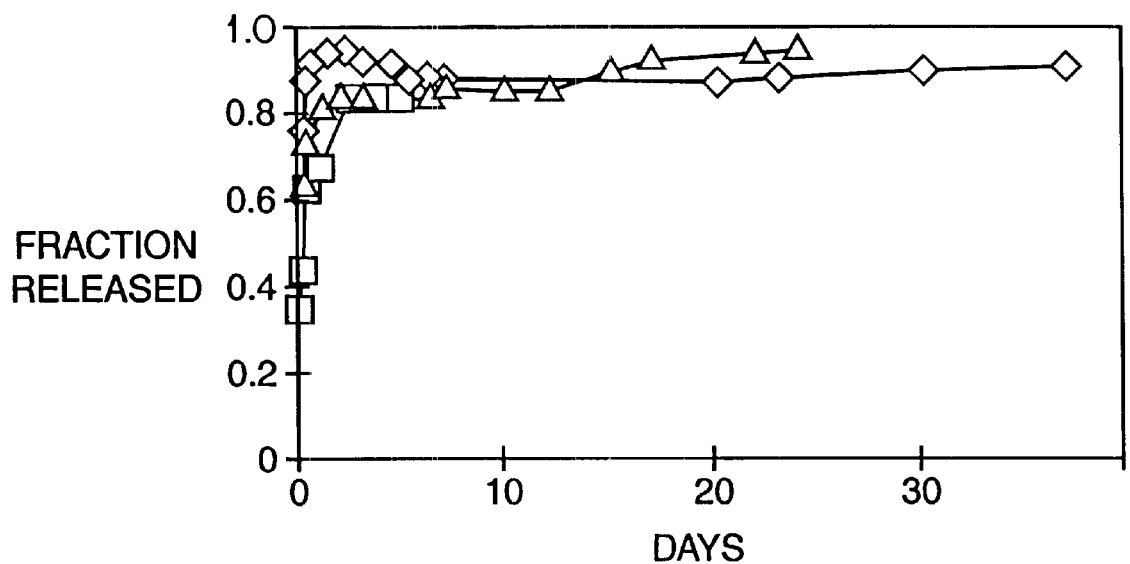
FIG. 10 shows release profiles of lidocaine hydrochloride PLGA formulations prepared by solvent extraction.

Cumulative release profiles for solvent evaporation and solvent extraction formulations are shown in FIGS. 9 and 10, respectively. In FIG. 9, lidocaine-PLGA microspheres prepared by solvent evaporation slowly released 5–15% of their contents during the first week. This release was followed by a continuous release during the initial stages. After 60 days, the hydrated microspheres had not significantly degraded. Factors contributing to the lag time before significant release was observed include the high molecular weight (70k–100k) g/mol) and hydrophobic nature of PLGA resulting in slow hydration of the microspheres. Also, SEM analysis showed product spheres to be relatively free of defects reducing the possibility of a burst release.

In FIG. 10, lidocaine hydrochloride-PLGA formulations prepared by solvent extraction essentially dumped 70–90% of their core load in the first 24 hours with complete release within days. The increased surface area of these smaller diameter microspheres and their high surface porosity observed by SEM contribute to the observed release, as well as the high aqueous solubility of the incipient lidocaine hydrochloride. It appears that lidocaine hydrochloride is mostly surface-bound in the microsphere formulations rather than homogeneously distributed throughout the polymer matrix.

Sustained release formulations releasing the. anesthetic lidocaine have been prepared by o/w solvent.evaporation techniques resulting in continuous release for 7–10 days following a one week, burst-free lag time. Conversely, lidocaine hydrochloride-PLGA formulations prepared by w/o solvent extraction completely emptied their contents within the first few days.

We claim:

1. A process for preparing controlled release microcapsule formulations characterized by burst-free, sustained, programmable release of non-steroidal, antiinflammatory drugs comprising:

dissolving a non-steroidal, antiinflammatory drug and a mixture of uncapped biocompatible, biodegradable poly (lactide/glycolide) polymer and end-capped biocompatible, biodegradable poly (lactide/glycolide) polymer in a volatile organic solvent, dispersing the dissolved mixture in an aqueous phase containing an emulsion stabilizer, and evaporating the organic solvent phase to obtain non-steroidal antiinflammatory drug-loaded microspheres.

2. A process for preparing controlled release microcapsule formulations characterized by burst-free, sustained, programmable release of non-steroidal, antiinflammatory drugs comprising:

dissolving a non-steroidal, antiinflammatory drug and a mixture of uncapped biocompatible, biodegradable poly (lactide/glycolide) polymer and end-capped biocompatible, biodegradable poly (lactide/glycolide) polymer in a polar organic solvent, dispersing the dissolved non-steroidal, antiinflammatory drug dissolved in a polar organic solvent in a non-polar organic phase, pouring the emulsion into a hydrocarbon solvent, extracting the polar organic phase into the hydrocarbon solvent to form microspheres.

3. A process of preparing a controlled release microcapsule formulation characterized by burst-free sustained programmable release of a long-acting local anesthetic comprising: dissolving the long-acting local anesthetic and a mixture of uncapped biocompatible, biodegradable poly (lactide/glycolide) polymer and end-capped biocompatible, biodegradable poly(lactide/glycolide) polymer in a volatile organic solvent, dispersing the long-acting local anesthetic and volatile organic solvent in an aqueous phase containing an emulsion stabilizer, and evaporating the volatile organic solvent to precipitate microspheres of long-lasting local anesthetic and poly(lactide/glycolide) microspheres.

4. The process of claim 1, wherein the biodegradable poly (lactide/glycolide) polymers comprise a ratio of lactide to glycolide from 100/0 to 50/50.

5. The process of claim 1, wherein said poly (lactide/glycolide) polymers have a molecular weight from 10–100 kDa.

6. The process of claim 1, wherein the end-capped polymer comprises terminal residues functionalized as esters and said end-capped polymer is hydrophobic.

7. The process of claim 1, wherein the uncapped polymer comprises terminal residues existing as carboxylic acids and said uncapped polymer is hydrophilic.

8. The process of claim 1, wherein the non-steroidal, antiinflammatory drug is selected from the group consisting of ibuprofen, florabioprofen, aspirin, acetaminophen, endocen, toridol, voltren, telecten, and ketoprofen.

9. The process of claim 8, wherein the non-steroidal, antiinflammatory drug is ketoprofen.

10. The process of claim 1, wherein said drug is evenly distributed through the poly(lactide/glycolide) matrix.

11. The process of claim 1, wherein said drug and said polymers comprise a homogeneous solid matrix.

12. The process of claim 2, wherein the biodegradable poly (lactide/glycolide) polymers comprise a ratio of lactide to glycolide from 100/0 to 50/50.

13. The process of claim 2, wherein said poly (lactide/glycolide) polymers have a molecular weight from 10–100 kDa.

14. The process of claim 2, wherein the end-capped polymer comprises terminal residues functionalized as esters and said end-capped polymer is hydrophobic.

15. The process of claim 2, wherein the uncapped polymer comprises terminal residues existing as carboxylic acids and said uncapped polymer is hydrophilic.

16. The process of claim 2, wherein the non-steroidal, antiinflammatory drug is selected from the group consisting of ibuprofen, florabioprofen, aspirin, acetaminophen, endocen, toridol, voltren, telecten, and ketoprofen.

17. The process of claim 6, wherein the non-steroidal, antiinflammatory drug is ketoprofen.

18. The process of claim 2, wherein said drug is evenly distributed through the poly(lactide/glycolide) matrix.

19. The process of claim 2, wherein said drug and said polymers comprise a homogeneous solid matrix.

20. The process of claim 3, wherein the local anesthetic is selected from the group consisting of tetracaine, lidocaine, etidocaine, carobicaine, xylocaine, marcaine, nesacaine, and etiod.

21. The process of claim 20, wherein the long-acting local anesthetic is lidocaine.

* * * * *